(12) United States Patent
Ghosh

(10) Patent No.: US 11,595,622 B2
(45) Date of Patent: Feb. 28, 2023

(54) SYSTEMS AND METHODS FOR DISTRIBUTED VIDEO MICROSCOPY

(71) Applicant: Inscopix, Inc., Palo Alto, CA (US)

(72) Inventor: Kunal Ghosh, Mountain View, CA (US)

(*) Notice: Subject to any disclaimer, the term of this patent is extended or adjusted under 35 U.S.C. 154(b) by 0 days.

(21) Appl. No.: 17/316,394

(22) Filed: May 10, 2021

(65) Prior Publication Data

US 2022/0094881 A1 Mar. 24, 2022

Related U.S. Application Data

(63) Continuation of application No. 16/809,991, filed on Mar. 5, 2020, now abandoned, which is a continuation of application No. 16/227,044, filed on Dec. 20, 2018, now abandoned, which is a continuation of application No. 15/687,166, filed on Aug. 25, 2017, now Pat. No. 10,200,657, which is a continuation of application No. 15/403,819, filed on Jan. 11, 2017, now abandoned, which is a continuation of application No. 13/761,875, filed on Feb. 7, 2013, now abandoned.

(60) Provisional application No. 61/597,670, filed on Feb. 10, 2012.

(51) Int. Cl.
*H04N 7/18* (2006.01)
*G02B 21/36* (2006.01)

(52) U.S. Cl.
CPC .......... *H04N 7/183* (2013.01); *G02B 21/365* (2013.01)

(58) Field of Classification Search
CPC ....... H04N 7/183; G02B 21/365; G16H 10/40
See application file for complete search history.

(56) References Cited

U.S. PATENT DOCUMENTS 7,015,444 B2 * 3/2006 Kawano ............... G02B 21/004
250/201.3

OTHER PUBLICATIONS

Parvin et al. "DeepView: A Channel for Distributed Microscopy and Informatics", 1999.*
Helmchen et al. "A Miniature Head-Mounted Two-Photon Microscope: High Resolution Brain Imaging in Freely Moving Animals", 2001.*

* cited by examiner

*Primary Examiner* — Michael E Teitelbaum

(57) ABSTRACT

System and methods are provided for distributed microscopy. A plurality of microscopes may capture images and send them to a media server. The microscopes and the media server may be part of a local area network. The microscopes may each have a distinct network address. The media server may communicate with an operations console, which may be used to view images captured by the microscopes. The operations console may also accept user input which may be used to selectively control the microscopes.

18 Claims, 4 Drawing Sheets

SYSTEMS AND METHODS FOR DISTRIBUTED VIDEO MICROSCOPY

CROSS-REFERENCE

This application is a continuation of U.S. patent application Ser. No. 16/809,991, filed Mar. 5, 2020, which is a continuation of U.S. patent application Ser. No. 16/227,044, filed Dec. 20, 2018, which is a continuation of U.S. patent application Ser. No. 15/687,166, filed Aug. 25, 2017 which is a continuation of U.S. application Ser. No. 15/403,819, filed, Jan. 11, 2017, which is a continuation of U.S. application Ser. No. 13/761,875, filed Feb. 7, 2013, which claims the benefit of U.S. Provisional Patent Application No. 61/597,670, filed Feb. 10, 2012, each of which applications is entirely incorporated herein by reference.

BACKGROUND OF THE INVENTION

Microscopes and related instruments are typically used to capture images of specimens. However, traditional image capture techniques are often time consuming and individualized. For example, in conventional microscopes, samples are loaded onto a microscope which captures an image of the sample, and then unloaded to make way for the next sample. Many applications exist where high throughput techniques would be beneficial for gathering information. However, the inefficiency of conventional microscopy methods would become increasingly cumbersome for high throughput systems. Additionally, typical microscope arrangements do not have an efficient way of handling information collected from a high throughput system.

A need exists for systems and methods for distributed microscopy that may be capable of simultaneously capturing images and/or image streams (e.g., videos) from a plurality of microscopes operating concurrently. A further need exists for systems and methods for handling information related to the captured images.

SUMMARY OF THE INVENTION

A network of microscopes may be operating concurrently on a Local Area Network (LAN). The network of microscopes may provide the ability to view individual video feeds in real-time, locally or remotely, and the ability to control individual microscopes (e.g., to adjust imaging parameters) over the network. Such an infrastructure may be inherently scalable and could be the "backbone" supporting distributed or massively-parallel video microscopy. The impact of distributed video microscopy for applications such as in vivo brain imaging in freely behaving subjects could be profound, enabling, for example, the running of behavioral assays in parallel for basic research (e.g., to run different control experiments, increase experimental throughput, etc.), and/or high throughput in vivo assays for drug screening.

An aspect of the invention may be directed to a system for distributed microscopy. The system may comprise a plurality of microscopes, each microscope capable of capturing an image and having a network address; a media server in communication with the microscopes over a local area network, wherein the microscopes are capable of simultaneously providing image data to the media server; and an operations console in communication with the media server, capable of displaying at least one image based on the image data.

A method for collecting a plurality of images may be provided in accordance with another aspect of the invention. The method may comprise capturing a plurality of images, using a plurality of microscopes, each microscope having a network address; providing data representative of the images simultaneously from the microscopes to a media server over a local area network; and displaying at least one image at an operations console in communication with the media network.

Other goals and advantages of the invention will be further appreciated and understood when considered in conjunction with the following description and accompanying drawings. While the following description may contain specific details describing particular embodiments of the invention, this should not be construed as limitations to the scope of the invention but rather as an exemplification of preferable embodiments. For each aspect of the invention, many variations are possible as suggested herein that are known to those of ordinary skill in the art. A variety of changes and modifications can be made within the scope of the invention without departing from the spirit thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

While preferred embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

The invention provides systems and methods for distributed video microscopy. Various aspects of the invention described herein may be applied to any of the particular applications set forth below or for any other types of microscopy or imaging systems. The invention may be applied as a standalone system or method, or as part of an integrated pre-clinical or clinical system. It shall be understood that different aspects of the invention can be appreciated individually, collectively, or in combination with each other.

Figure 1:
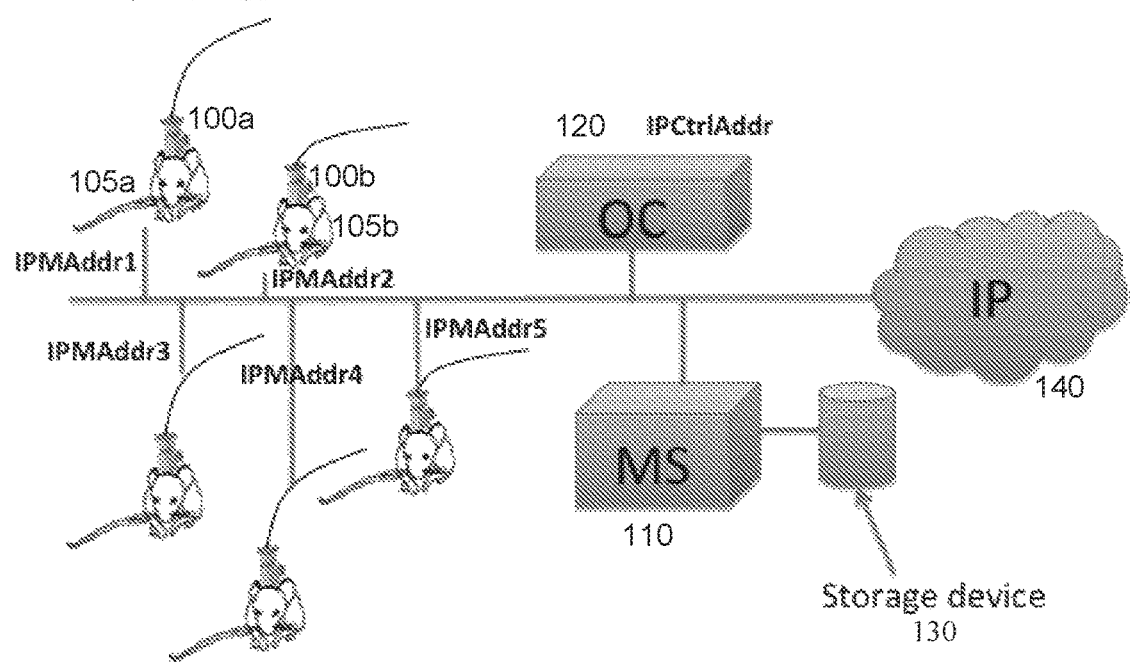
FIG. 1 shows an example of a network architecture for distributed video microscopy in accordance with an embodiment of the invention.

FIG. 1 shows an example of a network architecture for distributed video microscopy in accordance with an embodiment of the invention. One or more microscopes 100a, 100b may be part of the network architecture. The microscopes may be in communication with a media server 110 and/or an operations console 120. One or more storage device 130 may also be provided within the network architecture.

In some embodiments, one or more components of the network architecture may be operating as part of a local area network (LAN). For example, a network of microscopes 100a, 100b may be operating concurrently on a LAN. The media server 110, operations console 120, and/or storage device 130 may be part of the same LAN. In some instances, the LAN may be connected or connectable to another network 140. The other network may be a wide area network (WAN), such as the Internet, telecommunications network, data network, another LAN, or any other network. In some instances, a cloud-based network may be used. One or more components of the system or network architecture may have a cloud-computing based infrastructure. One or more components of the system (e.g., servers, storage devices) may reside in a cloud (e.g., physically at a remote off-site location or locations, or may be distributed over one or more locations).

A microscope 100a, 100b may be capable of providing images. The images may be provided to the media server 110. In some embodiments, the images may be stored in one or more storage device 130. In some instances, the images may be provided directly to the media server over the LAN or other type of network. Any description of a LAN may apply to any other type of network and vice versa. The images may be sent as data representations of the images. The data may be digital data. The images may also be provided to an operations console 120. The images may be provided directly to the operations console over the LAN, or may be provided to the operations console through the media server. For example, the images may be provided to the media server, which may provide images to the operations console. The media server may provide images to the operations console through the LAN, or through another network 140, such as the Internet.

The images provided by a microscope may be a static image (e.g., snapshot) or image stream (e.g., video). The images may be provided continuous (e.g., continuous video feed) or in a discontinuous (e.g., snapshots or videos taken at discrete times) manner. In some instances, the network of microscopes may provide the ability to view individual video feeds in real-time. The microscopes may be broadcasting the images. As the images are captured, the microscopes may transmit the images in real-time. The microscopes may target the recipient of the images, such as specific operation consoles, media servers, or other devices, or may broadcast in a manner where any number of recipients may receive the images.

The images provided by the microscope may have a high resolution. For example, the microscope may provide one or more images with a resolution of up to about 100 nm, 300 nm, 500 nm, 700 nm, 1 µm, 1.2 µm, 1.5 µm, 2 µm, 2.5 µm, 3 µm, 3.5 µm, 4 µm, 5 µm, 7 µm, 10 µm, 15 µm, 20 µm, 25 µm, 30 µm, 40 µm, 50 µm or 100 µm. The microscope may have any field of view. For example, the field of view may be greater than, less than, or equal to about 0.01 mm$^2$, 0.02 mm$^2$, 0.05 mm$^2$, 0.07 mm$^2$, 0.1 mm$^2$, 0.15 mm$^2$, 0.2 mm$^2$, 0.3 mm$^2$, 0.4 mm$^2$, 0.5 mm$^2$, 0.7 mm$^2$, 1.0 mm$^2$, 1.2 mm$^2$, 1.5 mm$^2$, 2 mm$^2$, 2.5 mm$^2$, 3 mm$^2$, 3.5 mm$^2$, 4 mm$^2$, 5 mm$^2$, 7 mm$^2$, or 10 mm$^2$.

The microscope may include one or more optical elements that will assist with obtaining the images. For example, the microscopes may include one or more lens, mirror, filter, dichroic, beamsplitter, or any other optical element. One or more objective lenses may be provided. The microscope may be capable of magnifying the subject, sample, or specimen being imaged. The optical element may permit light to pass through the optical element. The optical element may reflect all or a portion of the light. The optical element may filter the wavelengths of light or may alter the wavelengths of the light passing through or deflected by the optical element. One or more optical element may be movable with respect to another optical element and/or an illumination source. One or more optical element may be movable with respect to an object being imaged. The optical element may move automatically without intervention by a human. One or more fiberoptic element may or may not be used by the microscope.

An illumination light source may be provided. The illumination light source may be part of the microscope. Alternatively, the illumination source may be separate from the microscope. Light from the illumination light source may be provided to the object being imaged. Response light from the object being imaged may be provided to a light sensing arrangement. Response light from the object may be captured by an image capturing device. Light provided to the sample and/or from the sample may interact with one or more optical element. The light may be passed through, focused, dispersed, and/or reflected by one or more optical element. The light may be used to back-light the object being imaged, front-light the object being imaged, or side-light the object being imaged. Light from the illumination source may approach the object being imaged from any angle(s).

Some examples of illumination light sources may include light emitting diodes (LEDs) or organic light-emitting diodes (OLED). Other light sources such as lasers may be used.

The image may be captured by the microscope in a digital and/or analog format. One or more sensor array may be provided. In some instances, a camera may be provided to capture the image. The camera may be a still camera and/or a video camera. An image of the object being imaged may be captured in a single instance (e.g., snapshot, video), or portions of the object may be captured at a time. For example, a scanning technique may be utilized. Data representative of the captured image (such as static images or video) may be transmitted by the microscope. The data may be digital data. The data may or may not undergo pre-processing at the microscope. For example, the data may be compressed, encrypted, formatted, validated, or undergo any other pre-processing step on board the microscope. The microscope may have a processor that may be capable of performing one or more pre-processing step. In some instances, data compression may be useful for reducing bandwidth used by the microscope, which may be advantageous in high throughput situations.

The image captured by the microscope may be any type of image. For example, the image may include a visible image created by using visible light from the electromagnetic spectrum. The image may be a thermal image using infra-red radiation. In some instances, the image may capture a fluorescent reaction or may be created utilizing fluorescence microscopy. For example, epifluorescent imaging may be utilized, which may include the interaction between an excitation light and the target object, which may cause the generation of imaging fluorescence. The excitation light that reaches the object being imaged may have a wavelength that may be configured for absorption by one or more fluorophores. The fluorophores may emit light at different (e.g., longer or shorter) or the same wavelengths. In some instances, acoustic imaging, such as ultrasound may be utilized.

In some embodiments, the microscopes may be a miniature microscope. For example, the microscope may weigh less than or equal to about 100 grams, 50 grams, 40 grams, 30 grams, 20 grams, 15 grams, 10 grams, 7 grams, 5 grams, 3 grams, 2 grams, 1 gram, 700 mg, 500 mg, 300 mg, 100 mg, 50 mg, 30 mg, 10 mg, 5 mg, 3 mg, or 1 mg. The microscope may have a small footprint. For example, a microscope may have a footprint of about 10 cm$^2$ or less, 5 cm$^2$ or less, 4 cm$^2$ or less, 3 cm$^2$ or less, 2 cm$^2$ or less, 1 cm$^2$ or less, 0.5 cm$^2$ or less, 0.1 cm$^2$ or less, 0.05 cm$^2$ or less, or 0.01 cm$^2$ or less. The microscope may have a small volume. For example, the microscope may have a volume of about 50 cm$^3$ or less, 30 cm$^3$ or less, 20 cm$^3$ or less, 10 cm$^3$ or less, 5 cm$^3$ or less, 4 cm$^3$ or less, 3 cm$^3$ or less, 2 cm$^3$ or less, 1 cm$^3$ or less, 0.5 cm$^3$ or less, 0.1 cm$^3$ or less, 0.05 cm$^3$ or less, or 0.01 cm$^3$ or less.

One or more portions of the microscope described herein may be enclosed or partially enclosed in a housing of the microscope.

The microscopes may be used in in vivo applications. For example, the microscopes may be attached to a live being and/or image a portion of a live being while delivering the images over the network. In one example, the network architecture may include that the microscopes 100a, 100b are attached to a live being 105a, 105b while connected to a network, such as a LAN. The microscopes may be attached to the live being and/or image a portion of the live being while delivering the images over the network. In some embodiments, the microscopes may be used for in vivo brain imaging, and may be capturing images of the live beings' brains. The microscopes may be used for other imaging applications and may image other portions of the live beings. Other portions may include any bodily fluid, tissue or organs of the live beings. The imaged portions of the live beings may be subcutaneous. Alternatively, the imaged portions need not be subcutaneous. The imaged portions may include images of a subject's skin or surface tissue. In some instances, only a portion of the live being may be imaged. The microscope may be installed adjacent to or immediately over the portion of the live being that is imaged. The microscope may or may not be contacting the portion of the live being that is imaged. In some instances, a gap may be provided between the microscope and the portion of the live being that is imaged. A layer or barrier may or may not be provided between the microscope and the portion of the live being that is imaged. For example, skin or other tissue may or may not be provided between the portion being imaged. In some instances, an object being imaged may be underneath the layer, such as the skin. The object may be imaged through the skin or other layer.

The live beings may or may not be conscious as the images are being captured and/or delivered. The live beings need not be anesthetized while the images are being captured and/or delivered. In some instances, the live beings may be freely moving while the images are captured and/or delivered. The microscopes may be mounted on live beings. The microscopes may move with live beings as they move. The weight of the microscopes may be carried by the live beings. The microscopes may be moving or movable as the images are captured.

In some embodiments, a single microscope 100a may be attached to a live being 105a. Alternatively, any number of microscopes may be attached to a live being at a given time. For example, two or more, three or more, four or more, five or more, ten or more, or twenty or more microscopes may be attached to a live being at a given time and/or imaging a portion of the live being at a given time. Different microscopes may be used to image different regions or portions of the live being and/or the same regions or portions of the live being. The different microscopes may be simultaneously providing images over the network. For example, concurrent video feeds may be provided of the live being.

The live beings may include any animals, such as mice, rats, other rodents, dogs, cats, murines, or simians. In some instances, the live beings may be humans. In some embodiments, the live beings may be 25 grams or less, 50 grams or less, 100 grams or less, 500 grams or less, 1 kg or less, or 2 kg or less in weight. Images may be gathered from the live beings for pre-clinical or clinical testing. Images may be gathered from the live beings for diagnosis and/or treatment.

In some instances, the microscopes may be mounted on beings that were once alive. The microscopes may be mounted on dead beings. The microscopes may capture images a portion of the dead beings. The portions of the dead beings may or may not be subcutaneous.

The microscopes may be used to image live beings or non-live beings. For example, any type of sample, specimen, or subject may be imaged by the microscopes. The sample may have been removed from a being, such as a live being. Alternatively, any other sample, specimen or subject may be imaged. The imaged object may be in a solid state, liquid state, gaseous state, or any combination thereof.

Any number of microscopes may be provided on the network. In some embodiments, there may be one or more, two or more, three or more, five or more, ten or more, fifteen or more, 20 or more, 25 or more, 30 or more, 40 or more, 50 or more, 60 or more, 70 or more, 80 or more, 100 or more, 120 or more, 150 or more, 200 or more, 300 or more, 500 or more, or 1000 or microscopes connected over the network. Any number of microscopes, such as those described herein, may be connected over a LAN. This may advantageously provide high throughput image gathering. Any number of the microscopes may be capturing and/or delivering images concurrently. For example, all or some of the microscopes connected to the network may be capturing images and delivering them to the media server. The microscopes may continuously broadcast the images (e.g., provide continuous video feeds), or may provide the images in a staged or discrete manner.

Microscopes may be divided into one or more groups. Any number of microscopes may be provided in a group. The groups may or may not be of equal size. A single microscope may belong to any number of groups. For example, a microscope may belong to zero, one, two, three, four or more groups. Group designations may be specified by a user. The group designations may depend on the objects being imaged. For example, microscopes may be mounted on live beings. The microscope group designation may depend on a characteristic of the live beings. For example, microscopes mounted on live beings being treated with a particular drug with a particular dosage may belong to a particular group. Microscopes mounted on male live beings may be part of another group. These groups may or may not overlap. A user may be able to specify any number of groups, and may be able to specify which microscopes belong to each group.

Microscopes may have any locations. For example, all microscopes provided in the system may be at the same location (e.g., within the same facility, on the same premises, on the same floor, or within the same room). Alternatively, one or more microscopes may be at different locations (e.g., within different rooms, on different floors, in different buildings or facilities, on different premises, in different cities, in different countries, anywhere in the world). The microscopes may be capable of communicating over a global network. In some instances, microscopes within the same group may be at the same location, or may be at different locations. Multiple groups of microscopes may be provided at the same location, or distributed over different locations.

Global integration of microscopes may be possible. Microscopes may be networked together even if they are not at the same location. In some instances, a cloud-based network architecture may be used to permit microscopes distributed among physically disparate locations to be networked together. Other networks described may be used to permit microscopes located at various locations to be networked together.

Analytics may or may not be provided, which may assist the user with assigning zero, one, or more groups to a microscope. For example, if a microscope can not belong to two mutually exclusive groups, the system may notify a user, if the user tries to assign the microscope to both groups. For example, a microscope may not belong to both a first group of a particular dosage of a drug, and a second group with a different dosage of the drug.

In some instances, the number of microscopes that can be supported by the networked system may depend on a maximum data rate/channel, and available network bandwidth. Several optimizations can be performed to maximize number of microscopes on the network under the constraints of a certain maximum channel data rate and the available network bandwidth. For example, data transfer rates may be modulated depending on source and/or destination. Network priority levels may be assigned to each microscope, and changed, to preferentially allocate network resources to high-value data sources. In some instances, the resolution of the images provided by the microscopes may be varied depending on anticipated need. For example, if an image being transmitted by a microscope is detected to be depicting an object of interest, a higher resolution may be used, while other microscopes on the network transmit images at lower resolutions. One or more form of lossless or lossy data compression may be utilized. In some instances, data compression may depend on the image captured by the microscopes. In some instances, the frame rate of the image stream provided by the microscopes may be varied depending on anticipated need. For example, if an image stream being transmitted by a microscope is detected to be depicting a process of interest, a higher temporal resolution (frame rate) may be used, while other microscopes on the network transmit image streams at lower temporal resolutions.

The microscope 100a, 100b may be an integrated microscope that can be directly connected to the LAN. The microscope may be connected to the LAN in any manner. The microscope may be connected via a wired connection or a wireless connection. For example, the microscope may be connected to the network via a cable, such as a standard CAT5/CAT6 Ethernet cable. The microscope may be connected to the network via a wireless connection, such as a radio, microwave, or infra-red connection. Examples may include WiFi, Bluetooth, radiofrequency transmitters.

A microscope 100a, 100b may have its own network address (e.g., IPMAddr1 . . . n). For instance, the microscope may act as a node on the network with its own static Internet protocol (IP) address. Off-the-shelf components and open standards can be leveraged to develop custom hardware for the microscope to enable it to be plugged into a network and assigned an IP address (akin to a computer network card). In some embodiments, each microscope may have its own IP address. The IP address may be unique to the microscope within the LAN. The IP address may be unique to the microscope over a WAN. Each microscope may have a distinct network address, within the local system or within the global system. In alternate embodiments, each microscope may or may not have a network address. In some instances, one or more microscopes of a network may not have a network address and/or the network address may not be assigned. In some instances, a network address may not initially be provided to a microscope but may be assigned later on the fly. In some instances, network addresses may be assigned to a microscope as needed. One or more microscopes, which may or may not be each microscope of a system, may have a static network address that remains the same, or may have a dynamic network address that may be modified as needed on the fly. The network address of the microscope may permit a media server 110 to access the microscope. In some embodiments, a remote operations console may receive user input relating to the specific microscope.

The microscope may also have hardware that may permit images to be captured and sent to the network. For example, custom hardware may be provided, which may include a standard video codec, e.g., MJPEG or MPEG-4, and/or custom algorithms to compress acquired video imaging data and stream over the network to a media server. The image format utilized may be a commonly used format, or may be a specialized format for the system. One or more format conversion may be utilized.

Power can be delivered to each microscope over Ethernet. In some instances, power may be delivered to the microscope via a wired connection to a network. The microscope may or may not be solely powered by the network connection. Alternatively, the microscope may have a separate connection to a power source, such as a plug to a utility. In other embodiments, microscopes may have a local power source on-board. The on-board power source may be an energy storage source (e.g., battery, ultracapacitor), or an energy generation source (e.g., renewable energy source such as solar energy converter).

A microscope 100a, 100b may have one or more characteristic, component, or features of a microscope, as described in U.S. Patent Publication No. 2006/0028717, U.S. Patent Publication No. 2011/0122242, or U.S. patent application Ser. No. 13/218,181, which are hereby incorporated by reference in their entirety.

A media server 110 may be provided in a network in accordance with an embodiment of the invention. The media server may be connected to one or more microscopes over a LAN. The media server may be any device, which may include a server computer. The media server may have one or more processor and/or memory thereon. The memory may be capable of storing tangible computer readable media with code, logic, or instructions for performing one or more step or action described herein. The processor may be capable of performing the one or more step or action described herein. The media server may have a network communication unit that may connect the media server to the LAN. The media server may be connected to the network via a wired or wireless connection, such as those described herein. In some instances, a single media server may be provided for a LAN of microscopes. Alternatively, any of the features or duties described herein may be shared by a plurality of media servers that may be connected to the LAN. The plurality of media servers may communicate with one another over the LAN. The media server may or may not have its own network address, such as a static IP address.

The media server 110 may be capable of receiving the images (e.g., video feeds) from the microscopes. The media server may be able to receive images simultaneously provided by a plurality of microscopes. A plurality of images may be simultaneously streamed to the media server over a network. The media server may be a centralized server capable of communicating with any of the microscopes simultaneously. The media server also may be capable of communicating with a single selected microscope or a plurality of selected microscopes simultaneously.

The media server may process and/or store the images. In some instances, the images may be stored locally on the media server. Alternatively, an additional storage device 130 may be used. The additional storage device may be one or more databases, which may or may not be distributed over one or more network devices, which may include computers, servers, laptops, tablets, or mobile devices. The storage device may be directly accessible by the media server. The storage device may be a local storage device that may be connected directly to the media server or the LAN. In some alternative embodiments, the storage device may be capable of communicating with the media server over a WAN, such as the Internet. The storage device may or may not have its own network address, such as an IP address. The storage device network address may be unique within a LAN, or a WAN.

The incoming streaming microscope images (e.g., video feeds) may be managed by the media server 110. Video feeds can be delivered for immediate display and/or stored for future retrieval. In some instances, video feeds may be displayed at an operations console in real-time as they are provided to the media server. Peripherals such the storage device 130 and other computing resources can be directly linked to the media server.

In some instances, one or more therapeutic or drug delivery devices may be connected to the network. The therapeutic devices may be able to communicate with a media server directly or over a network. The therapeutic devices may be able to communicate with an operations console or other device directly or over a network, as described in greater detail elsewhere herein.

The architecture provided may support a multicast network. A media server may be capable of buffering a plurality of video feeds provided from the microscopes.

The media server may have a communications interface. The communications interface may permit the media server to communicate over a network. The communications interface may permit the media server to communicate with one or more microscopes, one or more drug delivery devices, one more additional servers, one or more operations consoles, one or more storage unit, or one or more peripherals. The communications interface may permit the media server to communicate with any external device directly or over a network. As previously described, the media server may also have a processor and a memory. The memory may store information, such as non-transitory computer readable media comprising code, logic, or instructions to perform one or more steps. The processor may be capable of performing one or more steps described herein. The processor may be specially programmed to perform one or more of the steps. For example, the processor may be capable of executing one or more step indicated by the non-transitory computer readable media. The processor may be capable of processing data from one or more sources, such as images from microscopes. The processor may create data that may be transmitted to an external device, such as an operations console or drug delivery device.

As previously mentioned, the media server may be capable of processing the images. For example, the media server may decrypt and/or encrypt the image data. For example, if the data provided from a microscope is encrypted, the media server may decrypt it. In another example, the media server may encrypt image data before sending it to another location, such as a storage device or an operations console.

The media server may also be capable of compressing and/or decompressing image data. In some instances, a microscope may pre-compress image data before sending it to the media server. The microscope may pre-compress image data to save network bandwidth. The media server may be capable of decompressing image data. Alternatively, the media server may compress data received from the microscope prior to sending it to another location, such as an operations console.

The media server may format the image data. The media data may cause the image data to be converted to a desired format. The desired format may be a commonly used image/video format. Alternatively, the desired format may be a specialized format. In some instances, a format may be selected depending on the expected recipient device. For example, if a media server is sending an image to an operations console, the image format or other characteristics of the image may be selected based on the type of operations console. For example, a different image format or other characteristic may be used when sending the image to a mobile phone versus a personal computer. The media server may be capable of selecting the proper image format and/or other characteristics and making the necessary changes to the data.

In some embodiments, the media server may be capable of performing analytics. One or more algorithms may be provided that may assist the media server with analyzing the image data. For example, the media server may note an anomaly or unusual portion of the image. Such an anomaly may be highlighted or zoomed. The media server may also note if an error appears to have occurred in capturing the image. For example, if the image shows up as all white or black instead of showing the expected image with its contrasts, an alert may be provided. The analytics may include making one or more measurement of portions of the captured images.

In some instances, the media server may perform analytics that may affect the subsequent operation of other external devices. For example, based on analysis of information received from the microscopes, the media server may provide instructions to a drug delivery device or other device. Alternatively, such analytics may be performed by another device that may receive data from the media server.

In some embodiments, an image captured by a microscope may affect the operation of another microscope. For example, feedback related to image data provided by a first microscope may be used to guide a second microscope. In some instances, analytics may occur on image data from the first microscope. One or more measurement may be made based on the image data from the first microscope. Such analytics and/or measurements may occur at the media server automatically without the intervention of a human. Alternatively, such analytics and/or measurements may occur at an operations console automatically without human intervention. In another example, a user may view image data from the first microscope and provide one or more instructions. Such analytics and/or instructions may depend on features of interest provided in the image. The analytics, measurements and/or instructions may be used to affect the second microscope. For example, the operations of the second microscope, such as the zoom, pan, resolution, focus, illumination, or any other feature may be affected.

Similarly, an image captured by a microscope may affect the operation of the same microscope. Feedback related to image data provided by a microscope may be used to guide the same microscope. In some instances, analytics may occur on image data from the microscope. One or more measurement may be made based on the image data from the microscope. Such analytics and/or measurements may occur at the media server automatically without the intervention of a human. Alternatively, such analytics and/or measurements may occur at an operations console automatically without human intervention. In another example, a user may view image data from the microscope and provide one or more instructions. The analytics, measurements and/or instructions may be used to affect the same or other microscopes. The operations of the microscope, such as the zoom, pan, resolution, focus, illumination, or any other feature may be affected. A microscope's operation can be adjusted in real-time. The operation may be adjusted in real-time automatically without requiring any human intervention, or may be adjusted in response to user instructions. The adjustments may occur in real-time based on feedback from analyses being performed on the data being fed to the network. The analyses may occur with the aid of a processor. The processor may perform a part of or the entirety of the analyses. Alternatively, a user may perform part of or the entirety of the analyses. Decisions may be made on the fly and a microscope's operation may be adjusted based on data collected by the microscope and/or images (such as videos) observed.

A media server may provide a centralized repository that may manage the image data from the plurality of microscopes. The media server may gather information from a plurality of microscopes, and may affect the operation of microscopes based on the gathered information. The operation of a microscope may be based on information gathered about that microscope, another microscope, another group of microscopes, or any combination thereof. Auto-adjusting and/or remote adjusting may be useful in high throughput systems, where data gathered from a group of microscopes can be used to make adjustments to any selected microscopes. Such adjustments may beneficially utilize the intelligence gathered from simultaneous processing. Such adjustments may also assist with improving quality of images captured through the microscopes.

A network may also include an operations console 120. The operations console may act as a user's gateway to the microscope image feeds and for configuration and control. The operations console may have a processor and memory. The operations console may have a screen or other user interaction device. In some instances, the operation console may have a touchscreen. A user may be able to view information on the operation console, e.g., through a screen. The operations console may accept user input (e.g., via keyboard, mouse, pointer, trackball, joystick, touchscreen, voice command, gesture command/camera, or any other user interactive device). The operations console may authenticate the user, manages access to image feeds, and/or may provide an interface to issue commands to control individual microscopes or groups of microscopes.

In some embodiments, only authorized users may be permitted to access the images. In some embodiments, a use may be authenticated and determined whether the user is authorized to access the images. The operations console may receive a user input to authenticate the user. The user input may be a password, biometrics, voice recognition, or any other sort of authenticating information from the user.

The operations console 120 backend may handle administrative functions and its frontend may be a user interface for the network of microscopes, i.e., consists of image viewers displaying microscope video feeds and modules for individual microscope control and online video analytics. The operating console user interface can be web-based, allowing for remote access to video feeds. Examples of such frontend functionality may be described in greater detail elsewhere herein.

Any network device may be used as an operations console. For example, an operation console may be a device, such as a server computer, personal computer, laptop, tablet, mobile device (e.g., smartphone, cellular phone, personal digital assistant), or any other network device.

The operations console may be connected directly to the LAN. The operations console may communicate with the media server. The operations console may or may not directly communicate with the microscopes. In some instances, a server/client relationship and architecture may be provided between the media server and the operations console. The operations console may communicate with the media server over a network, such as the LAN, or a WAN such as the Internet. FIG. 1 shows an example where the operations console is connected to the media server over the LAN. The operations console may have its own network device, such as a static IP address (e.g., IPCtrlAddr).

The operations console may permit local or remote communication with the microscopes. The operations console may permit a user to view image feeds from the microscopes and/or control the operation of the microscopes. The user may or may not be in the same location (e.g., same room or building) as the microscopes.

Figure 2:
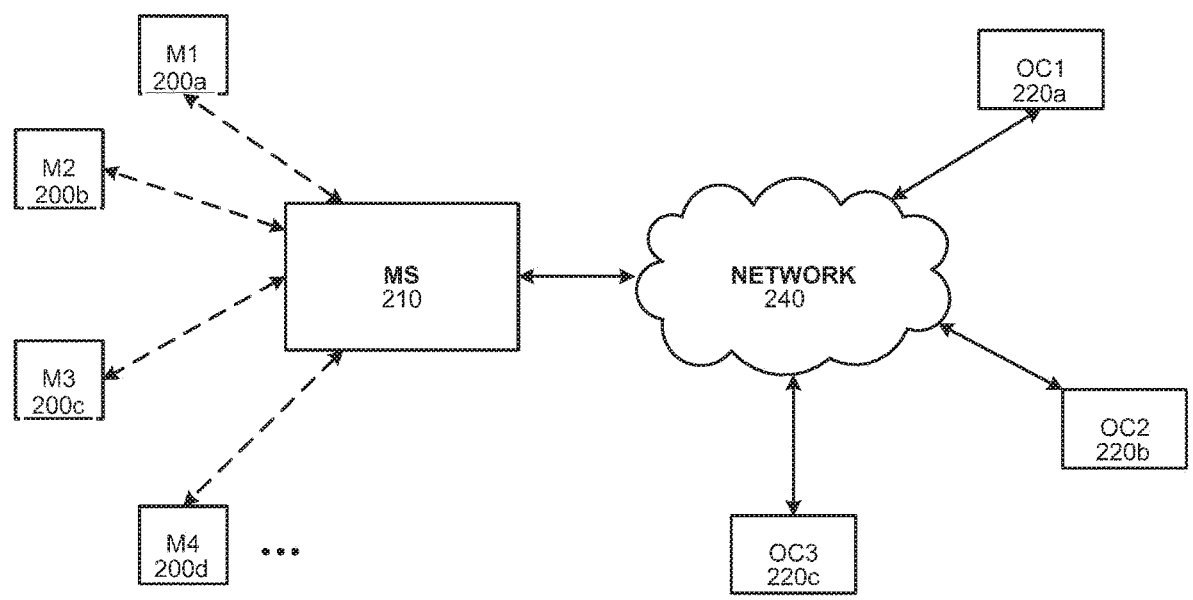
FIG. 2 provides an additional example of a system for distributed video microscopy.

FIG. 2 provides an additional example of a system for distributed video microscopy. A plurality of microscopes (e.g., M1, M2, M3, M4, . . . ) 200*a*, 200*b*, 200*c*, 200*d* may communicate with a media server 210. The microscopes may communicate with the media server over a LAN. In some instances, the microscopes may communicate with the media server over a hardwired or wireless connection. The microscopes may each have their own network address, such an IP address, that may permit each microscope to be individually controllable or accessible.

In some embodiments, one-way communication may be provided between the microscopes and the media server. For example, the microscopes may send images to the media server. Or the microscopes may receive instructions from the media server. In other embodiments, two-way communications may be provided between the microscopes and media server. The microscopes may send data, such as image data, to the media server. The media server may send data, such as instructions, to the microscopes. Individual network addresses for the microscopes may assist with the communications between the microscopes and the media server. For example, the network addresses may indicate to the media server which microscope the data arrived from. Similarly, when instructions are provided to one or more microscopes, the network addresses may be used to ensure the selected microscope(s) receive the instructions.

The media server 210 may be capable of communicating with one or more operations console 220a, 220b, 220c. The media server may communicate with the operations consoles over a network 240. In some instances, the network may be a WAN, such as the Internet. In other embodiments, the network may be a LAN. In some instances, an operations console may be provided as part of the LAN over which the media server may communicate with the microscopes (e.g., as shown in FIG. 1). In other instances, the operations console is not part of the LAN, but is provided over a separate network (e.g., as shown in FIG. 2).

Video feeds and data can be encrypted when sent outside the LAN, such as for remote access. In one embodiment, such data may be encrypted when sent over a network 240, such as a WAN. The data may be encrypted when provided to a remote operations console. The data may or may not be encrypted when sent over the LAN (e.g., when sent from a microscope to a media server or local operations console, or vice versa). In some instances, the encryption may be performed using the media server. Other data manipulation such as validation, compression, formatting may occur at the media server.

A user may be able to communicate with a media server through an operations console. The operations console may be a dedicated operations console, or may be selectively utilized as an operations console. One or more users may be able to communicate with the media server through one or more operations consoles. Any number of operations consoles may be used to access the media server. For example, one or more, two or more, three or more, five or more, ten or more, twenty or more, fifty or more, 100 or more, 200 or more, 500 or more, or 1000 or more operation consoles may communicate with the media server. The operation consoles may be communicating with the media server simultaneously or any number of operation consoles may be communicating with the media server at any given time.

In some embodiments, an operations console may or may not have a software and/or application downloaded that may assist with communications with the media server. A software and/or application may assist with viewing microscope feeds and/or controlling the microscopes. In some instances, the operations console may communicate with the media server via a web browser. The web browser may display a web page or user interactions that may enable a user at the operations console to interact with the microscopes.

In some embodiments, any device may be or become an operations console. For example, a personal computer, laptop, server, tablet, or mobile device may be an operations console when it is communicating with the media server.

An operations console may permit a user to access the microscopes locally or remotely, and may provide the ability to control individual microscopes (e.g., to adjust imaging parameters) over the network. A user may be able to view image feeds from the microscope through the operations console. A user may be able to view the image feeds in real-time. For example, a microscope may capture an image, and deliver an image, which may be sent to a media server, which may send the image to the operations console. This may happen in real-time. Less than 5 seconds, 3 seconds, 2 seconds, 1 second, 0.5 seconds, or 0.1 seconds may elapse between the microscope capturing the image and the operations console displaying the image to a user.

In some instances, each of the feeds from the operating microscopes may be displayed to the user simultaneously. Alternatively, the user may select which feeds the user wishes to view. In some instances, a user may view a feed from a single selected microscope, or may view a plurality of feeds from a plurality of selected microscopes. In some instances, the microscopes may be arranged into groups. A user may select to view feeds from a selected group or plurality of selected groups of microscopes. The feeds from the selected microscopes may be viewed simultaneously. They may be viewed simultaneously in a continuous fashion. Alternatively, there may be a staggering or rotation of views provided. For example, if eighteen microscopes are providing feeds, and there is room on a screen of the operations console for 6 simultaneous views, the images may be rotated so that 3 different rounds of six images are provided. Images may be rotated or staggered in any order and with any timing. A user may be able to select the number of separate microscope feeds to be displayed simultaneously and/or the timing or order of such displays.

Figure 3:
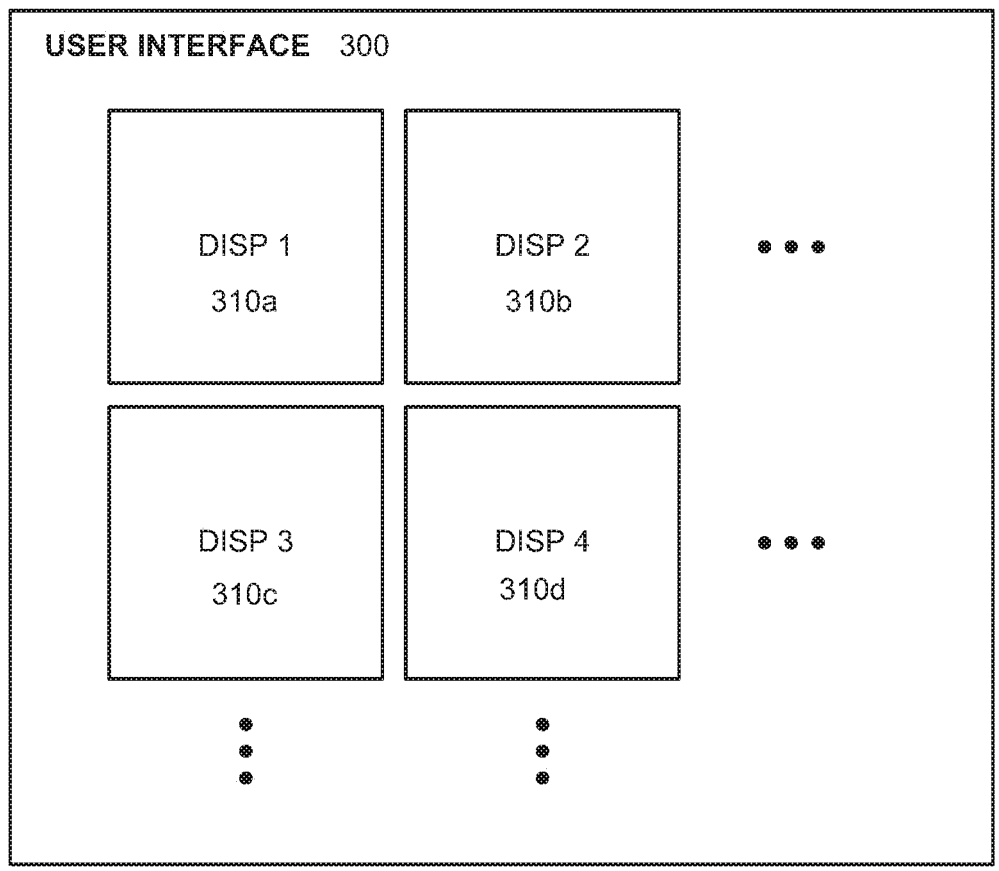
FIG. 3 illustrates an example of a user interface capable of simultaneously displaying multiple image feeds in accordance with an embodiment of the invention.

FIG. 3 illustrates an example of a user interface capable of simultaneously displaying multiple image feeds in accordance with an embodiment of the invention. A user interface 300 may be displayed on an operations console. For example, a user interface may be displayed on a screen of an operations console. The user interface may be displayed in a web browser or may be displayed as part of a software or application running on the device.

One or more microscope image feed 310a, 310b, 310c, 310d may be viewable on the user interface 300. In some instances, a plurality of microscope image feeds are viewable simultaneously. The image feeds may be arranged in one or more row and/or one or more column. In some instances, an array of image feeds may be displayed. Alternatively, the image feeds may be displayed in any manner. The image feed displays may all be the same size and/or shape or may have varying sizes and/or shapes. In some instances, a set of thumbnail image or menu or images may be provided. A user may select one or more of the thumbnail image to view an expanded display of the selected image.

A user may select individual microscopes and/or groups of microscopes by name or by network addresses. For example, the user may enter one or more IP addresses to view feeds from the selected microscopes having the entered IP addresses. Alternatively, the user may enter a microscope name, number, graphical representation, or other identifier that may correspond to the one or more IP addresses, in order to view feeds from the selected microscopes. A user may be capable of selecting one or more microscopes to be controlled and/or to receive an instruction.

An operations console may also enable a user to remotely control one or more selected microscopes. For example, through the operations console, a user may be able to zoom, pan, adjust excitation light, or select field of view for the one or more selected microscopes. A microscope may zoom in or out, increase or decrease the field of view, pan laterally, adjust a scanning pattern, turn an excitation light on or off, adjust the brightness or intensity of an excitation light, select one or more excitation light source, adjust a wavelength of an excitation light, adjust a focus of the microscope, or perform any other action in response to instructions from a user via the operations console. The user may provide an instruction through the operation console to the media server, which may provide the instructions to the selected one or more microscopes, thereby causing the microscope to respond to the user commands. One or more components of a microscope may be actuated in response to user commands. Electrical signals may be provided to and within the microscope in response to user commands.

A media server may be able to communicate with an operations console in real-time. For example, instructions from an operation console may be delivered to a microscope in real-time and/or a microscope may respond to the instructions in real-time. In some instances, less than 5 seconds, 3 seconds, 2 seconds, 1 second, 0.5 seconds, or 0.1 seconds may elapse between receiving the instructions at the operations console and the microscope reacting to the instructions.

A user may individually select images to respond to commands. For example, the user may enter network addresses or identifiers corresponding to individual networks. Alternatively, a user may pre-designate one or more groups of microscopes. The user may enter identifiers corresponding to individual groups. All the microscopes in the group may respond to the user commands. For example, the user may enter a command to zoom in, causing all microscopes within the group to zoom in.

An operations console may also permit a user to interact with the image data provided by the one or more selected microscopes. A user may elect to record image feeds from one or more selected microscopes; erase feeds from the one or more selected microscopes; or rewind, pause/freeze, play, or fast forward feeds from selected microscopes. A user may be able to edit an image. For example, the user may be able to zoom, crop, balance an image (e.g., brightness, contrast, color), sharpen, blur, or any other tool with the image.

Embodiments and infrastructure described herein may be inherently scalable and could be the "backbone" supporting distributed or massively-parallel video microscopy. The system may be capable of handling high throughput microscopy.

Figure 4:
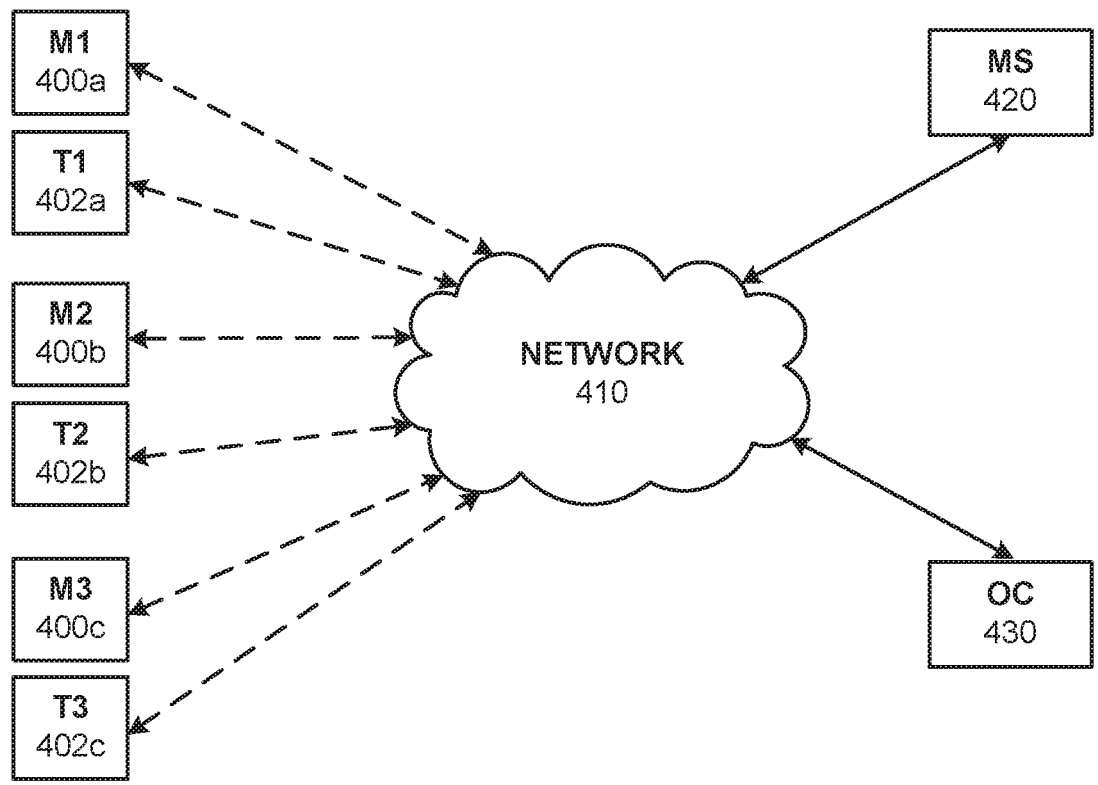
FIG. 4 provides an example of a system for distributed microscopy with drug delivery capabilities.

FIG. 4 provides an example of a system for distributed microscopy with drug delivery capabilities. One or more microscopes 400a, 400b, 400c may be able to communicate over a network 410. A media server 420 and/or operations console 430 may also be able to communicate over the network. In some instances, additional external devices, such as therapeutic/drug delivery devices 402a, 402b, 402c may be able to communicate over the network. As previously described, the network may be any type of network, such as a cloud-based network, LAN, WAN, or any other type of network.

The system described herein may be capable of delivering drugs remotely over-the-network. In some instances, one or more drug delivery device/mechanism 402a, 402b, 402c may be provided at an imaging site. In some instances, each of the microscopes 400a, 400b, 400c may have or be at the same site as one or more corresponding drug delivery mechanism. Alternatively, zero, one, two or more of the microscopes of the system may have or be at the same site as one or more corresponding drug delivery mechanism. In some instances, one or more of the microscopes need not have or be at the same site as one or more corresponding drug delivery mechanism. A drug delivery device and/or mechanism may be integrally formed with the microscope, or may be a separate component or device from the microscope. In some instances, the drug delivery device or mechanism may be at each subject being imaged by a microscope. For example, a microscope may be attached to a live being. The drug delivery device may be configured to deliver drugs to the same live being. The drug delivery device may deliver drugs to the live being at the site that is imaged, or another site.

In some instances, the microscopes may be used to image an imaging site that need not be in a live being. For example, the imaging site may be imaging a well or micro-well. The drug delivery mechanism may be capable of delivering a drug to the same imaging site or another component in communication with the imaging site. For example, the drug delivery mechanism may be capable of delivering the drug directly to a well being imaged, or to another site that fluidically provides the drug to the well being imaged.

In one example, a drug delivery device or mechanism may include a syringe with a network-connected actuator. The drug delivery device may deliver drugs subcutaneously (e.g., via needle or microneedle(s)), topically, via aerosol, intravenously, or any other mechanism known in the art. The drug delivery device may deliver a drug to a target site. The target site may or may not be imaged by the microscopes. The target site may be part of a live being that is imaged by the microscopes. The target site may be capable of affecting an imaging site imaged by the microscopes.

The network-based control system may permit adjustment of the drug delivery device(s) remotely. For example, a user at an operating console or remote instance of an operator console can, based on the imaging data feed, remotely adjust the amount of drug being delivered to a subject (e.g., at the imaging site or a part of the subject). In some instances, a user may provide instructions on whether to start drug delivery, stop drug delivery, or alter dosage of drug delivery. In some instances, a drug delivery device or mechanism may provide a single drug or multiple drugs. The user may be able to remotely control the individual or multiple drugs delivered. The user may provide such instructions in real-time while viewing data, or at other times. The drug delivery device may respond in real-time, or in accordance with predetermined schedules. The user may or may not be in the same room, floor, facility, premises, city, or country as the drugs being delivered.

In alternate embodiments, the determination for drug delivery may be made with aid of a processor. For instance, based on analysis of the image data, a processor may automatically provide instructions to start drug delivery, stop drug delivery, or alter dosage of drug delivery, of a single drug or multiple drugs. The processor may make adjustments on a predetermined schedule, in response to one or more detected events, or in real-time. In some instances, observations, drug delivery adjustments, and feedback may occur in real-time. For instance, microscopes may capture images of a region which may be affected by drug delivery, instructions to vary or maintain drug delivery may be provided, the reaction may be imaged and based on such reaction further instructions to vary or maintain drug delivery may be provided.

In some instances, the system may include additional external devices that may communicate over a network. For example, additional external devices may be capable of communicating with a media server and/or operations console directly or over a network. The external devices may affect a site being imaged by one or more microscopes. The additional external devices may share one or more characteristics of the drug delivery devices mentioned herein or vice versa. For example the external devices may include light sources, heating or cooling sources, pressure controlling systems, moisture or humidity controlling systems, actuation or movement systems, or sample transfer systems. Such additional external devices may be controlled by a user who may or may not be remotely located, or by a processor.

Distributed microscopy may be useful for in vivo and in vitro applications. In some embodiments, in vivo imaging of an organism may include imaging portions of the organism. For example, tissue, organs, fluid, or any other portion of the organism may be imaged. In some embodiments, in vivo brain imaging may be conducted using a distributed microscopy system. For instance, cerebellar vermis may be imaged to study microcirculation concurrently with locomotive or other behaviors by mounting the microscope on the cranium of the organism. By mounting a microscope on a conscious live being, and simultaneously imaging the brain or other portions of the organism, various active processes of the live being may be studied. Correlations between particular behaviors of the live being and brain activity, or other activity of the organism may be made using imaging. Additional examples of in vivo applications may include high-throughput drug screening in animal models of disease. Various genetic animal disease models exist, for example, for brain diseases such as autism, Parkinson's, and schizophrenia. Multiple microscopes imaging disease processes in animal disease models and normal processes in animal controls may provide statistically-relevant datasets leading to an understanding of the causal mechanisms of disease. In some instances the same infrastructure of multiple microscopes imaging diseased and control animals concurrently may be used to test the efficacy of new drug compounds in stemming disease progression. Additional examples of in vitro applications may include monitoring cellular and tissue assays in parallel, for example, to study and identify early-stage drug candidates. Other in vitro applications may include imaging and transmitting digital images from several pathology workstations, with each workstation comprising of a microscope imaging a tissue sample on slide. The distributed video microscopy may have applications in the areas of biology, chemistry, genetics, pharmacology, environmental, or any other areas.

The impact of distributed video microscopy for in vivo brain imaging could be profound, enabling applications ranging from running behavioral assays in parallel for basic research (e.g., to run different control experiments, increase experimental throughput, etc.), to enabling high throughput in vivo assays for drug screening.

The ability to deliver drugs or perform other actions in a massively parallel environment may also be advantageous in in vivo and in vitro applications. For example, the ability to deliver drugs remotely over the network may be important for high-throughput in vivo or in vitro drug screening applications. The ability to view imaging data and react quickly may save a large amount of time and manpower in various screening applications.

Such applications may permit a large amount of information to be collected in a parallel fashion. This may be useful for studies, research, or other information gathering applications where images are collected from a large number of subjects and/or samples, and/or over a period of time.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents.

What is claimed is:

1. A system for distributed microscopy, comprising:
a media server in communication with a plurality of microscopes over a network, wherein the media server is configured to receive data simultaneously from the plurality of microscopes, wherein each microscope of the plurality of microscopes: (1) is configured to capture an image of an imaging site; (2) has a network address; and (3) has a volume of 50 cubic centimeters or less; and
one or more processors in communication with the media server, configured to (i) analyze image data from the image of the imaging site captured by each microscope; (ii) designate the plurality of microscopes into two or more groups according to the respective network address of each of the plurality of microscopes; and (iii) transmit an operation command to a group of the two or more groups of microscopes or to one or more devices associated with the group of microscopes, wherein the operation command is selected based at least in part on the image data, wherein the media server may note an anomaly or unusual portion of the image.

2. The system of claim 1, wherein the operation command causes the group to zoom in on the anomaly.

3. The system of claim 1, wherein the operation command causes the group to highlight the anomaly.

4. The system of claim 1, wherein the media server notes an error in capturing the image.

5. The system of claim 4, wherein the operation command causes the group to correct the error.

6. The system of claim 4, wherein the operation command causes the processor to generate an alert message.

7. The system of claim 4, wherein the error in capturing the image comprises an issue with contrast.

8. The system of claim 1, wherein the operation command causes a change in one or more of: zoom, pan, resolution, frame rate, focus, or illumination of the image as captured by the plurality of microscopes.

9. A system for distributed microscopy, comprising:
a media server in communication with a plurality of microscopes over a network, wherein the media server is configured to receive data simultaneously from the plurality of microscopes, wherein each microscope of the plurality of microscopes: (1) is configured to capture an image of an imaging site; (2) has a network address; and (3) has a volume of 50 cubic centimeters or less; and
one or more processors in communication with the media server, configured to (i) process image data from the image of the imaging site captured by each microscope; (ii) designate the plurality of microscopes into two or more groups according to the respective network address of each of the plurality of microscopes; and (iii) transmit an operation command to a group of the two or more groups of microscopes or to one or more devices associated with the group, wherein the operation command is selected based at least in part on the image, wherein the media server formats the image data.

10. The system of claim 9, wherein the media server formats the image data based on an expected recipient device.

11. The system of claim 9, wherein the media server makes one or more measurements based on the image.

12. The system of claim 9, wherein operation command comprises causing a change or maintenance in operation of another microscope.

13. The system of claim 9, wherein operation command causes the group to change a zoom level of the image.

14. The system of claim 9, wherein operation command causes the group to change a pan of the image.

15. The system of claim 9, wherein operation command causes the group to change a resolution of the image.

16. The system of claim 9, wherein operation command causes the group to change a focus of the image.

17. The system of claim 9, wherein operation command causes the group to change an illumination level of the image.

18. The system of claim 9, wherein operation command causes the group to change a frame rate of the image.

* * * * *